United States Patent
Xie et al.

(10) Patent No.: US 7,717,000 B2
(45) Date of Patent: May 18, 2010

(54) ISOKINETIC SAMPLING

(75) Inventors: Cheng-gang Xie, Sawston (GB); Ian Atkinson, Ely (GB); Paul Hammond, Bourn (GB); Gary Oddie, St. Neots (GB); Paul Bolchover, Cambridge (GB)

(73) Assignee: Schlumberger Technology Corporation, Ridgefield, CT (US)

( * ) Notice: Subject to any disclaimer, the term of this patent is extended or adjusted under 35 U.S.C. 154(b) by 746 days.

(21) Appl. No.: 10/573,619

(22) PCT Filed: Sep. 9, 2004

(86) PCT No.: PCT/GB2004/003849

§ 371 (c)(1),
(2), (4) Date: Nov. 28, 2006

(87) PCT Pub. No.: WO2005/031311

PCT Pub. Date: Apr. 7, 2005

(65) Prior Publication Data

US 2007/0193373 A1    Aug. 23, 2007

(30) Foreign Application Priority Data

Sep. 29, 2003    (GB) .............................. 0322702.2

(51) Int. Cl.
    *G01N 1/20* (2006.01)
(52) U.S. Cl. .................................................. 73/863.03
(58) Field of Classification Search .. 73/863.02–863.03
    See application file for complete search history.

(56) References Cited

U.S. PATENT DOCUMENTS 3,840,051 A    10/1974    Akashi et al.

(Continued)

FOREIGN PATENT DOCUMENTS

EP    0 561 557 A1    9/1993

(Continued)

OTHER PUBLICATIONS

Nakazatomi & Sekoguchi 'Effect of pressure on entrainment flow rate in vertical upwards gas-liquid annular two-phase flow. Part I: experimental results for system pressures from 0.3MPa to 20 MPa' Heat Transfer, Japanese Research, vol. 25 (5), 1996, pp. 267-280.

(Continued)

*Primary Examiner*—Thomas P Noland
(74) *Attorney, Agent, or Firm*—James McAleenan; Vincent Loccisano; Brigid Laffey (57) ABSTRACT

A method of sampling a multi-phase fluid stream is provided which comprises the steps of: sampling, with a sampling probe, a portion of the fluid stream; measuring the flow rate of said sampled portion; and measuring, independently of the sampling step, the total flow rate of the fluid stream, wherein the flow rate of the sampled portion is controlled according to the ratio of the flow rate of the sampled portion to the flow rate of the fluid stream, in order to obtain substantially isokinetic sampling of the fluid stream. The method may provide isokinetic sampling to an accuracy of 5% or less and preferably only samples a small portion of the fluid stream. The method has particular application for high rate condensate gas wells. A corresponding sampling system is provided which has particular application in the sampling of streams from wellheads. A flow conditioner for use with sampling methods and systems is also provided, the flow conditioner being a pipe section including: a swirl inducing section; a flow straightener; and an orifice plate.

19 Claims, 9 Drawing Sheets

U.S. PATENT DOCUMENTS

| | | | |
|---|---|---|---|
| 4,060,001 A * | 11/1977 | Archerd | 73/863.11 |
| 4,167,117 A | 9/1979 | Stokley et al. | |
| 4,301,679 A | 11/1981 | Boyle et al. | |
| 4,429,581 A | 2/1984 | Furmaga | |
| 4,522,218 A * | 6/1985 | Konak | 73/863.03 X |
| 4,566,342 A | 1/1986 | Kurz | |
| 4,574,643 A | 3/1986 | Scott et al. | |
| 4,776,210 A | 10/1988 | Baillie et al. | |
| 4,881,412 A | 11/1989 | Northedge | |
| 4,891,969 A | 1/1990 | Wayland et al. | |
| 5,309,946 A | 5/1994 | Ligneul | |
| 5,337,595 A * | 8/1994 | Lewis | 73/23.31 |
| 5,535,632 A | 7/1996 | Kolpak | |
| 5,654,502 A | 8/1997 | Dutton | |
| 5,762,107 A | 6/1998 | Laws | |
| 5,811,696 A * | 9/1998 | Jobson | 73/863.03 |
| 5,861,561 A | 1/1999 | Van Cleve et al. | |
| 5,894,080 A | 4/1999 | Dybdahl | |
| 6,041,668 A | 3/2000 | Guieze et al. | |
| 6,062,092 A | 5/2000 | Weaver | |
| 6,128,962 A | 10/2000 | Marrelli et al. | |
| 6,546,809 B1 * | 4/2003 | Andreussi | 73/861.04 |

FOREIGN PATENT DOCUMENTS

| | | |
|---|---|---|
| EP | 0 690 292 A2 | 1/1996 |
| EP | 0 690 292 A3 | 1/1996 |
| EP | 0 764 236 B1 | 8/2001 |
| GB | 2 041 035 A | 9/1980 |
| GB | 2 272 766 A | 5/1994 |
| GB | 2 275 990 A | 9/1994 |
| GB | 2 277 990 A | 11/1994 |
| GB | 2 299 167 A | 9/1996 |
| GB | 2 301 297 A | 12/1996 |
| GB | 2 311 606 A | 10/1997 |
| GB | 2 333 372 A | 7/1999 |
| WO | WO 91/08444 A1 | 6/1991 |
| WO | 95/22400 A1 | 8/1995 |
| WO | 98/12532 A1 | 3/1998 |
| WO | 98/12533 A1 | 3/1998 |
| WO | 98/33051 A1 | 7/1998 |
| WO | 00/47870 A1 | 8/2000 |
| WO | 00/49370 A1 | 8/2000 |
| WO | 01/77489 A1 | 10/2001 |
| WO | 02/20944 A1 | 3/2002 |

OTHER PUBLICATIONS

Kool et al 'Testing of gas condensate reservoirs- sampling, test design and analysis' SPE paper 68668, pp. 1-16 Asia Pacific Conference, Jakarta, Indonesia Apr. 2001.

Dybdahl et al 'A systematic approach to sampling during well testing' SPE paper 69427, pp. 1-15 SPE Latin American and Caribbean Conference, Argentina, Mar. 2001.

Theuveny et al 'Multiphase flowmeter application for well and fiscal allocation' SPE paper 76766, pp. 1-12 SPE Western Regional/ AAPG Pacific meeting, Alaska, May 2002.

Jayawardane et al 'PVT sampling with multiphase flowmeters- theoretical justifications and field limitations' SPE paper 77405, pp. 1-11 SPE Technical Conference, Texas, Oct. 2002.

Combined Search and Examination Report under Sections 17 and 18 (3) by the United Kingdom Patent Office dated Jan. 31, 2007 for Application No. GB 0700674.5.

* cited by examiner

ISOKINETIC SAMPLING

This application claims the benefits of priority from:
i) Application Number 0322702.2, entitled "ISOKINETIC SAMPLING," filed in the United Kingdom on 29 Sep. 2003; and
ii) Application Number PCT/GB2004/003849, entitled "ISOKINETIC SAMPLING," filed under the PCT on Sep. 9, 2004;

All of which are commonly assigned to assignee of the present invention and hereby incorporated by reference in their entirety.

BACKGROUND OF THE DISCLOSURE

The present invention relates to isokinetic sampling. It is particularly, but not exclusively, related to methods and apparatuses for carrying out isokinetic sampling, and in particular isokinetic sampling in oilfield applications.

In oilfield applications, as in many other fields, it is important to be able to analyse the composition and properties of a multi-phase fluid stream, such as a gas-condensate stream or a wet-gas stream. In particular it is desired to know the quantity of the various phases of the flow, for example by knowing the gas-oil ratio (GOR) or the condensate-gas ratio (CGR). It is also desired to know the properties of the various phases, for example their pressure, volume and temperature (PVT) relationships.

For example, the prediction of fluid phase behavior and reservoir simulation models based on equations-of-state (EOS) typically requires high quality PVT data.

PVT data are also often needed for flow assurance in wells and transport lines.

Furthermore, PVT data often have a significant impact on processing facility designs and specifications, and therefore on the profitability of gas-oil field.

However, to accurately determine the PVT properties and composition of reservoir fluid, representative fluid samples are required. Common analysis sampling procedures suffer from deficiencies in either or both of their accuracy and their ability to cope with high flow rates.

For example, a high-rate gas condensate well producing 5-100 MMscf (Millions standard cubic feet)/day with a gas-oil ratio of 3 k-100 k scf/bbl (CGR from 0 to 200 bbl/MMscf) (bbl=barrel of liquid; 1 m$^3$=6.29 bbl), can often overwhelm a test-separator, causing liquid carry-over in the separator gas outlet line, thereby providing poor measurement of the GOR and non-representative PVT samples (if the carry-over is not measured and corrected for). This normally also results in poor recombination ratios. Gas condensate wells are particularly problematic for sampling as large volumes of gas are associated with only small volumes of liquid, and the phase behavior will be highly sensitive to the quantity and composition of the liquid phase.

Wellhead sampling is therefore considered to be the only practical method of obtaining reliable test data for such applications. Isokinetic sampling at a wellhead of a multiphase fluid is desirable since, if achieved, it means that the sample of the fluid is at the same pressure, temperature and velocity as the main flow stream, and therefore will have identical properties to that main flow stream.

Figure 1:
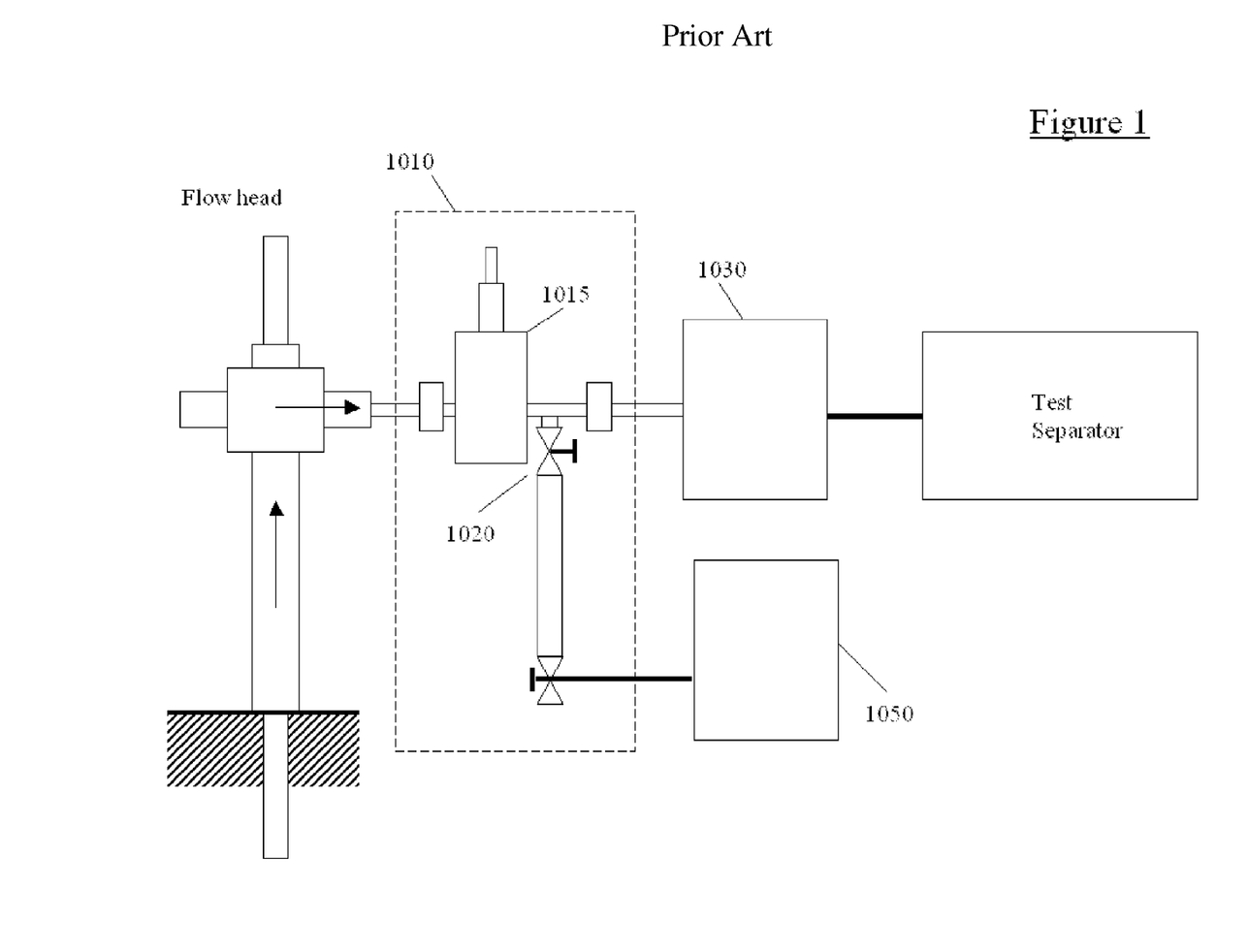
FIG. 1 is a schematic illustration of a known wellhead sampling system, and has already been described.

A known wellhead sampling system is shown schematically in FIG. 1, which is taken from Dybdahl and Hjermstad "A systematic approach to sampling during well testing", Society of Petroleum Engineers (SPE) paper 69427, SPE Latin America & Caribbean Petroleum Engineering Conference, Buenos, Argentina, 25-28 Mar. 2001 (see also the paper by Henk et al. "Testing of gas condensate reservoirs—sampling, test design and analysis", SPE paper 68668, SPE Asia Pacific Oil & Gas Conference, Jakarta, Indonesia, 17-19 Apr. 2001). Such a system is, for example, produced by Petrotech under their IsoSplit™ wellhead sampling and separator sampling services.

The wellhead sampling system of FIG. 1 consists of two parts.

Figure 2A:
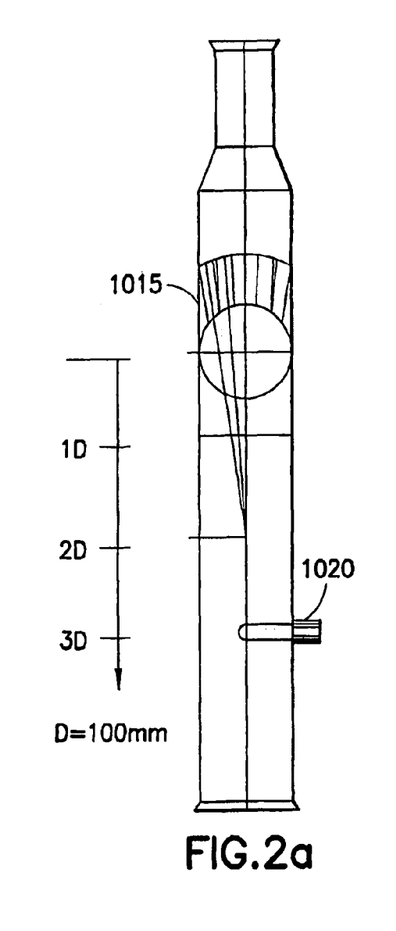
FIG. 2a is a schematic illustration of a flow-focusing mixer similar to that shown in GB 2301297 the prior art and has already been described.

The first part is a wellhead mixing/sampling manifold 1010, which is positioned upstream of the choke manifold 1030, and has a focusing-action static mixing device 1015 (see GB 2301297 & U.S. Pat. No. 5,894,080; a similar mixing device is shown in FIG. 2a) for collecting liquid at the wall of the pipe and distributing it into the main flow stream. A sampling probe 1020 is radially inserted downstream of the mixer 1015 for withdrawing a sample of the main flow stream.

The second part is an on-site laboratory 1050 (also called a "Mini-lab"), which processes the sampled stream to measure the condensate-gas ratio (CGR). PVT samples for compositional characterization are taken.

Figure 2B:
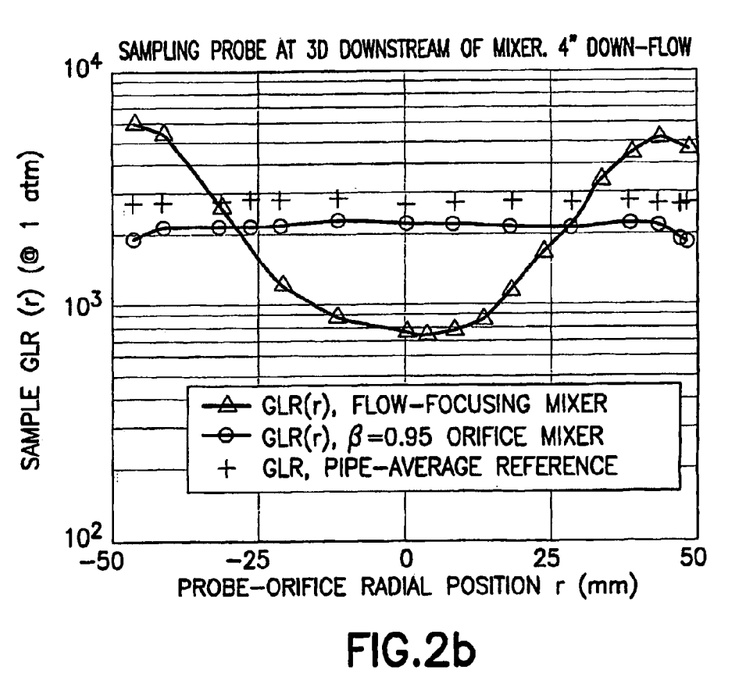
FIG. 2b shows the GLR cross-pipe profiles downstream of the mixer of FIG. 2a and downstream of a flow conditioner according to an embodiment of the present invention.

As described in SPE paper 68668, the liquid distribution across the flow pipe of FIG. 1 will vary, and either a mixing device or a traversing probe has to be used in order to have a split stream sample with the correct gas condensate ratio. As described in SPE paper 69427, the probe traversing enables sampling at multiple points across the pipe and the subsequent correction for the droplet and velocity distribution. It is stated in SPE 68668 that the liquid collected from the wall by the focusing-action mixer 1015 is distributed homogeneously into the flowing gas stream. However, our own gas-liquid ratio (GLR) profile measurement shown in FIG. 2b, for a mixer design (shown in FIG. 2a) similar to the focussing-action mixer 1015, indicates a liquid-rich jet at the central region of the sampling cross section. The GLR measured at such points will be a gross under-estimate of the pipe average value. FIG. 2b shows a −70% error in the GLR at the pipe centre, with respect to the pipe reference GLR.

SPE paper 68668 also states that sample withdrawal through the sampling probe 20 from the main stream is performed at an isokinetic sampling rate, i.e. at the same linear velocity as the wellhead fluid stream, which is necessary to sample the gas and liquid phase in the correct ratio. This isokinetic sampling rate is said to be calculated from the probe size and the gas flow rate measured at the test separator.

This approach has at least the following disadvantages:

1) A test separator is needed for wellhead sampling operations, which is bulky and expensive (FIG. 1).
2) The test separator can be overwhelmed by high-rate gas wells, leading to liquid carry-over in the separator gas outlet line. This can result in an inaccurate main-stream gas rate measurement used to set the isokinetic sampling rate.
3) The main-flow gas rate can fluctuate, for example due to changes in the liquid loading. This unsteadiness in the main flow rate can cause the separator gas rate measurement to be unreliable (see SPE paper 76766, by B. C. Theuveny and P. Mehdizadeh "Multiphase flowmeter application for well and fiscal allocation", Alaska, 20-22 May 2002), leading to unreliable isokinetic sampling.
4) Isokinetic sampling rate control based on measured main-stream gas flow rates can lead to errors when liquid loading becomes relatively high.

WO00/49370 describes a method for measuring the liquid and gas flow rates of a multi-phase fluid stream including withdrawing a portion of the overall flow rate under "isokinetic conditions". The sampled portion forms approximately 5% to 15% of the total flow rate.

The methods and apparatus disclosed in WO00/49370 do not independently measure the main flow stream, but instead derive measurements of the main flow stream from the effect of the sampling operation on the flow stream. Furthermore, although the methods described are claimed to be "isokinetic", this term is applied to all sampling in which the ratio of the sampled flow rate to the calculated total flow rate is within 20% of the ratio of the cross sectional area of the sampling probe to the cross sectional area of the flow stream. Adjustment of the sampling conditions is only made if the ratio falls outside this range.

The method proposed in WO00/49370 for measuring the total flow rate ($Q_1$) of the fluid stream is given in equation (5) of that application, with $Q_1$ being calculated as the sole unknown in the equation $$\frac{\Delta p_1}{\Delta p_2} = \left(\frac{Q_1}{Q_1 - q}\right)^2,$$

where q is the measured sampled flow rate and $\Delta p_1$ and $\Delta p_2$ are measured pressure differences of the main flow stream with and without sampling operating. This assumes that the density of the sampled flow q is the same as the density of the total flow $Q_1$.

Thus $Q_1$ is calculated as $$Q_1 = q \frac{\sqrt{\Delta p_1 / \Delta p_2}}{\sqrt{\Delta p_1 / \Delta p_2} - 1}.$$

From this equation, the error $\delta Q_1$ in $Q_1$ can be determined as $$\left(\frac{\delta Q_1}{Q_1}\right)^2 = \left(\frac{\delta q}{q}\right)^2 + \left(\frac{\delta P}{P} \frac{1}{P-1}\right)^2,$$

where $P = \sqrt{\Delta p_1 / \Delta p_2}$. For $P \gg 1$, $$\frac{\delta Q_1}{Q_1} \approx \frac{\delta q}{q}.$$

However, as $$\sqrt{\Delta p_1 / \Delta p_2} \to 1, \frac{\delta Q_1}{Q_1} \to \infty.$$

Therefore, in order to avoid excessive errors in the measurement of the total flow rate $Q_1$ when using the method of WO00/49370 it is important that the difference between $\Delta p_1$ and $\Delta p_2$ is large, and consequently that the flow rate of the sampled flow is a substantial proportion (i.e. more than 5%) of the total flow rate. When such sampling proportions are used in high flow situations, for example in a high-rate gas condensate wells, they can overwhelm the separator, or alternatively require a larger, and therefore more expensive separator.

BRIEF SUMMARY OF THE DISCLOSURE

The present invention is at least partly based on the realisation that isokinetic sampling from a fluid stream can be achieved by monitoring the ratio of the flow rate of the sampled flow to the total flow rate of the main fluid stream and adjusting the sampling rate accordingly. Contrast this with WO00/49370 which provides no suggestion that any repeated or continuous adjustment to achieve isokinetic sampling should be carried out, and indeed assume that sampling is carried out under isokinetic conditions in order to measure the total flow rate.

Thus, a first aspect of the present invention provides a method of sampling a multi-phase fluid stream comprising the steps of:

sampling, with a sampling probe, a portion of the fluid stream;

measuring the flow rate $Q_S$ of said sampled portion; and measuring, independently of the sampling step, the total flow rate Q of the fluid stream, wherein the flow rate of the sampled portion is controlled according to the ratio of the flow rate of the sampled portion to the flow rate of the fluid stream, in order to obtain substantially isokinetic sampling of the fluid stream.

Preferably the flow rate of the sampled portion is controlled such that the equation $$\frac{Q_S}{Q} = \frac{A_{probe}}{A_{pipe}}$$

is satisfied to within 10%, more preferably to within 5%, where $A_{probe}$ and $A_{pipe}$ are the respective cross-sectional areas of the sampling probe opening and the fluid stream at the sampling point.

The flow rates Q and $Q_S$ may be mass flow rates, and the flow rate $Q_S$ of the sampled portion of the fluid stream is preferably less than 0.2% of the total flow rate Q, more preferably less than 0.05% of the total flow rate Q.

The method may be used in high-rate gas condensate wells, where the gas flow rate is at least 5 MMscf/day. In wells with higher flow rates, the flow rate of the sampled portion of the fluid stream is particularly preferred to be a small proportion of the total flow rate so that downstream analytical processes on the sampled portion are not overwhelmed. An advantage of the present invention is that it can be used to sample relatively small proportions of the total flow.

Preferably the method further includes the step of separating said sampled portion into a sampled liquid flow and a sampled gas flow, and said step of measuring the sampled flow rate includes measuring the flow rate of the sampled liquid flow and the flow rate of the sampled gas flow. Either or both of these sampling flows may be measured using a Coriolis flow meter. This allows more accurate measurement of the flow rates of the different phases of the fluid stream. A Coriolis flow meter also allows the density of the flow to be measured.

In certain embodiments the step of measuring the total flow rate includes measuring the density of the fluid stream. The step of measuring the total flow rate may include measuring a differential pressure, which may, for example, be measured using a Venturi meter, or be an impact pressure measured using a Pitot tube.

Preferably the step of measuring the total flow rate is carried out continuously or repeatedly during the sampling process.

Preferably the step of controlling the flow rate of the sampled portion is carried out continuously or repeatedly during the sampling process.

The continuous or repetitive measuring of the total flow rate and controlling of the flow rate of the sampled portion allows correction of the flow rate of sampled portion in response to changes in the mass flow rate of the main flow stream.

In this respect, the term "continuous" also includes repeated discrete applications of the measuring and controlling steps above at regular intervals, these intervals being shorter than the time scale over which significant changes in the total mass flow rate of the main stream occur.

The above method is particularly applicable where the fluid stream is a feed from a well-head, and may be carried out at a well-head site.

Preferably the method further includes, prior to sampling the fluid stream, the step of conditioning the fluid stream.

Another aspect of the present invention provides a sampling apparatus for a multiphase fluid stream which can carry out the method of the above aspect.

According to this aspect, the present invention provides a sampling apparatus for sampling a multi-phase fluid stream, comprising:

means for measuring the total flow rate Q of the fluid stream;

a sampling probe for sampling a portion of said fluid stream;

a meter for measuring the flow rate $Q_S$ of said sampled portion; and a controller adapted to control the flow rate of the sampled portion according to the ratio of the flow rate of the sampled portion to the total flow rate of the fluid stream, in order to obtain substantially isokinetic sampling of the fluid stream.

Preferably the controller is adapted to control the flow rate of the sampled portion such that the equation $$\frac{Q_S}{Q} = \frac{A_{probe}}{A_{pipe}}$$

is satisfied to within 10%, more preferably to within 5%, where $A_{probe}$ and $A_{pipe}$ are the respective cross-sectional areas of the sampling probe opening and the fluid stream at the sampling point.

Flow rates Q and $Q_S$ may be mass flow rates, in which case the meter is a mass flow rate meter.

Preferably the cross-sectional area of the sampling probe opening is less than 0.2% of the cross-sectional area of the fluid stream at the sampling point, and thus the flow rate of the sampled portion is a similar fraction of the total flow rate of the fluid stream. More preferably the cross-sectional area of the sampling probe opening is less than 0.05% of the cross-sectional area of the fluid stream at the sampling point.

The sampling apparatus may form part of a high-rate gas condensate well wherein the gas flow rate is at least 5 MMscf/day.

Preferably the apparatus further includes a separator for separating the sampled portion into a sampled liquid flow and a sampled gas flow; a meter for measuring the flow rate of the sampled liquid flow; and a meter for measuring the flow rate of the sampled gas flow. Either or both of these meters may be Coriolis flow meters.

In some embodiments the means for measuring the total flow rate may include a densitometer for measuring the density of the fluid stream. The means for measuring the total flow rate may additionally or alternatively include a differential pressure sensor, such as that for use with a Venturi meter or a Pitot tube.

Preferably the means for measuring the total flow rate operates continuously or repeatedly during the sampling process.

Preferably the controller controls the flow rate of the sampled portion continuously or repeatedly during the sampling process.

Preferably the sampling probe is made from damage resistant material such as tungsten carbide or cobalt alloy, so that the cross sectional area of the sampling probe opening does not vary during the sampling process.

The sampling probe is preferably located in the centre of the pipe section.

Preferably the sampling apparatus further includes a flow conditioner located upstream of the sampling probe.

The fluid stream may be a feed from a well-head.

In order to achieve representative isokinetic sampling of a multi-phase stream using sampling at a single sampling point, it is preferable that, at the designated sampling cross-section of the pipe, the cross-pipe GLR profile is uniform.

Previously flow-focussing mixers have been used to try to provide such a uniform GLR profile. Examples of such mixers are plug-valve mixers, for example as shown in GB 2301297 and U.S. Pat. No. 5,894,080. A similar mixer to that in GB 2301297 is shown schematically in FIG. 2a. Where similar reference numerals are used in FIG. 2a, they refer to features already described in association with FIG. 1.

However, use of flow-focussing mixers, such as the mixer 1015 shown in FIG. 2b, can result in too much liquid being entrained into the central pipe region as a result of the focussing action of the mixers. At low pressures there may be excessive liquid jetting, leading to very non-uniform cross-pipe GLR and a large GLR error. FIG. 2b shows the GLR cross-pipe profile for air/water flows with an equivalent CGR of ~60 bbl/MMscf gas (gas rate $q_g \approx 1400$ m³/h or about 1.2 MMscf/day), and shows that the measured GLR has an error of approximately −70% from the reference value at the pipe centre.

It is anticipated that as the wellhead pressure increases, the GLR cross-pipe non-uniformity will improve as a results of the reduction in the gas-liquid density contrast, and hence in the gas-liquid velocity slip. However, the adverse effect of liquid jetting will still remain, even at high wellhead pressures. Similar results are expected to be seen with the plug-valve type mixers referred to above.

Therefore a further aspect of the present invention provides a flow conditioner for a wellhead sampling system, the flow conditioner being a pipe section including: a swirl inducing section; a flow straightener; and an orifice plate.

To achieve accurate isokinetic sampling at wellhead at a single sampling point, it is preferable to have a uniform cross-pipe GLR profile at the designated sampling cross-section. For annular or annular-mist flows prevailing in a wellhead sampling system (i.e. not fully developed vertical upward or downward flow), this can be achieved by removing liquid film from the pipe wall and by entraining it homogeneously in the gas core. It is also preferable that liquid drop re-deposition onto the pipe wall should be negligible at the sampling cross-section. Drop size is preferably small thereby minimizing gas-drop velocity slip and the rate of drop deposition. These factors will lead to a more representative sampling of gas and liquid flow rates, and hence a better measure of the GLR.

The creation of the initial swirl, upstream of the orifice plate, preferably creates a uniformly circumferentially distributed liquid film on the wall of the pipe section. The orifice plate sheds any such liquid film on the pipe wall back into the gas flow. After the initial formation of a liquid rich core downstream of the orifice plate, turbulence causes good mixing of the liquid and gas phases. Straightening the flow of the gas core prior to the orifice plate reduces the amount of liquid that is redeposited onto the pipe wall after shedding by the orifice plate. Therefore a relatively uniform cross-pipe GLR can be achieved, making it less important where on the pipe diameter in the sampling cross section a sampling probe is placed.

The swirl inducing section may include a tangential input to the pipe section. Alternatively the swirl inducing section may include a helical insert inside the pipe section.

The flow straightener is preferably located in the centre of the pipe section and such that there is an annular gap between the flow straightener and the wall of the pipe section, thereby straightening the gas core of the fluid stream whilst not affecting any liquid film located on the wall of the pipe.

The orifice plate may have a diameter of its open section which is between 0.85 and 0.95 of the local diameter of the pipe section, preferably between 0.9 and 0.95 of the local diameter of the pipe section (also referred to as the diameter ratio $\beta$).

The pipe section may narrowed at the orifice plate. The narrowed pipe section gives a higher gas flow momentum and higher gas Weber number.

To improve CGR measurement accuracy of lean gas condensate wells (CGR=0 to 50 bbl/MMscf), a dual-orifice mixer arrangement is preferably used for reducing liquid rate under-sampling at low liquid loadings.

In one example of such an arrangement, the first (i.e. upstream) orifice plate has a diameter ratio such as $\beta_1=0.9$, and the second orifice plate has a diameter ratio such as $\beta_2=0.95$. The two orifice plates may be axially separated by 1D to 3D, where D is the basic diameter of the pipe at the orifice plates.

The first, upstream orifice plate (diameter ratio $\beta_1$) is intended to shed as much as liquid to the pipe centre as possible (with a relatively small β-ratio); whilst the second orifice plate is used to shed any relatively thin liquid film that might be caused by the re-deposition of the liquid drops shed by the first orifice plate, after travelling a few pipe diameters.

A sampling probe may be used to sample the fluid stream, and is preferably located downstream of the orifice plate(s). More preferably the sampling probe is located at a distance between 1D and 3D downstream of the downstream orifice plate, where D is the diameter of the pipe section at the orifice plate (not the diameter of the orifice plate itself).

Preferably the sampling probe is located in the centre of the pipe section.

Another aspect of the present invention provides a method for conditioning the flow of a multi-phase stream comprising the steps of successively:

forming a liquid film at the wall of a pipe section which carries the fluid stream;

straightening the flow of at least a core of the fluid stream; and shedding the liquid film into said core.

Preferably the liquid film is substantially uniformly circumferentially distributed on the pipe wall.

The step of shedding the liquid film may use at least one orifice plate. The or each orifice plate may have an open diameter of 0.85 to 0.95 of the diameter of the pipe section in which it is placed, preferably between 0.9 and 0.95 of the diameter of the pipe section. The pipe section may narrow at least the orifice plate.

The step of forming the liquid film may include causing the fluid stream to swirl about the axis of the pipe section. Such rotary motion may be achieved by, for example, tangentially introducing the fluid stream to the pipe section, or by passing the fluid stream through a helical insert inside the pipe section.

Preferably the step of straightening the core of the fluid stream does not straighten a portion of the fluid stream adjacent to the walls of the pipe, and therefore does not affect the liquid film.

The fluid stream may be sampled using a sampling probe, the sampling preferably taking place downstream of the orifice plate(s). More preferably the sampling probe is located at a distance between 1D and 3D downstream of the downstream orifice plate, where D is the diameter of the pipe section at the orifice plate (not the diameter of the orifice plate itself).

Preferably the sampling probe is located in the centre of the pipe section.

The flow conditioner or method of the above two aspects may be used with the sampling methods and apparatuses of the earlier aspects to improve the accuracy of the isokinetic sampling.

BRIEF DESCRIPTION OF THE DRAWINGS

Embodiments of the present invention will now be described in relation to the accompanying drawings, in which.

DETAILED DESCRIPTION

Figure 3:
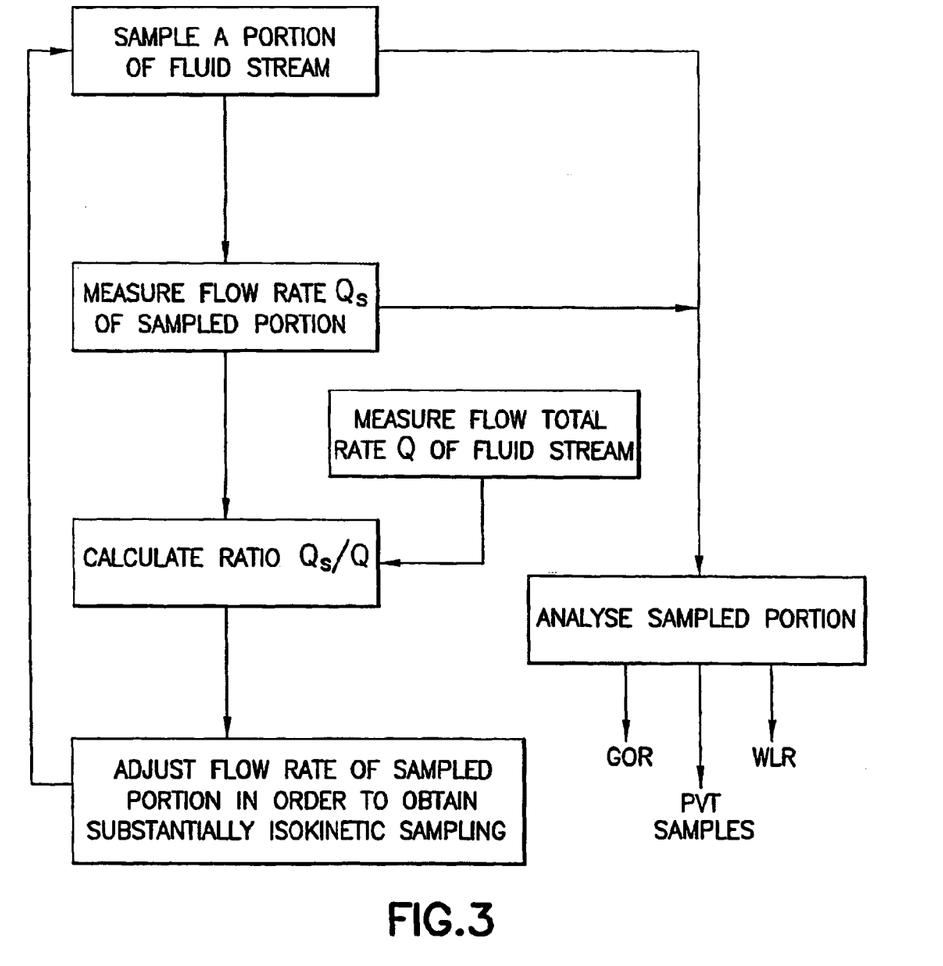
FIG. 3 is a flow chart showing a method according to an embodiment of the present invention.

Elements of a method of sampling according to an embodiment of the present invention are shown in the flow chart of FIG. 3.

A portion of a fluid stream is sampled, and the flow rate $Q_S$ of that sampled portion measured. The total flow rate Q of the fluid stream is also independently measured, and the ratio of the two measured flow rates calculated. Based on this ratio, the sampling flow rate (i.e. the proportion of the fluid stream which is sampled) is adjusted in order to substantially obtain isokinetic sampling conditions. This process is preferably either repeated or carried out continuously throughout the sampling process.

The sampled portion may be analysed concurrently with the flow rate measurements and adjustments, for example to provide the GOR, the WLR and samples for PVT analysis. This analysis may also use the flow rate measurement of the sampled portion.

Figure 4:
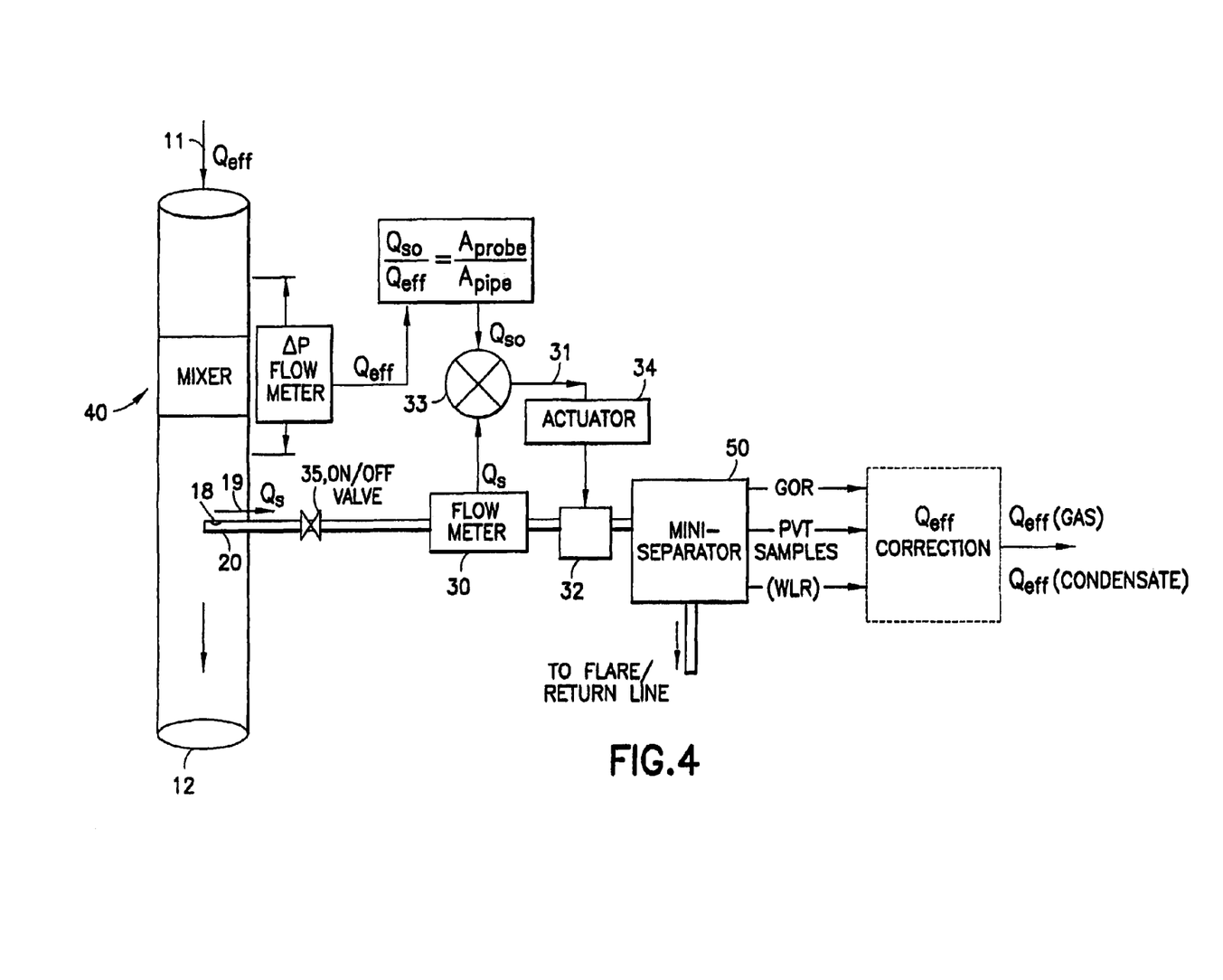
FIG. 4 is a schematic illustration of an isokinetic sampling system according to an embodiment of the present invention.

FIG. 4 shows an isokinetic sampling system according to an embodiment of the present invention.

An isokinetic sampling model is used to calculate the target sampling flow rate $Q_{SO}$, according to the main stream flow rate $Q_{eff}$. One example of such an isokinetic sampling model is $$\frac{Q_{So}}{Qeff} = \frac{A_{probe}}{A_{pipe}}$$

for substantially uniform mixed flow.

In contrast to the method described in relation to FIG. 1 above, in the present embodiment, the main stream flow rate $Q_{eff}$ is measured on-line in the pipe by a main pipe flow meter 40. This may be, for example, a Venturi or an orifice meter. The measured $Q_{eff}$ is then fed into the sampling model so that $Q_{SO}$ is updated as $Q_{eff}$ varies.

When the on/off valve 35, allowing sampling to take place, the actual sampling flow rate $Q_S$ is measured by a sampling flow meter 30 positioned in the sampling line. The actual sampling flow rate $Q_S$ and the target sampling flow rate $Q_{SO}$ are compared in comparator 33, which creates a flow control signal 31, on the basis of which control valve 32 is adjusted by the actuator 34 so as to keep $Q_S = Q_{SO}$.

Alternatively flow control signal 31 may be created as a result of a direct comparison between the main stream flow rate $Q_{eff}$ measured by the main pipe flow meter 40 and the sampling flow rate $Q_S$ measured by the sampling flow meter.

The main pipe flow meter 40 of the embodiment of FIG. 4 may be positioned upstream or downstream of a mixer or other flow conditioner (not shown). In certain embodiments, the main pipe flow meter will also serve as a good gas-liquid mixer, and so a separate flow conditioner may not be required.

However, use of a flow conditioner upstream of a flow meter 40 can serve to eliminate or substantially reduce the gas-liquid velocity slippage for the flow passing through the main pipe flow meter 40, thereby allowing a homogenous flow model (e.g. standard single-phase Venturi equations) rather than a slip-model (e.g. a 2-layer, separated model for annular or annular-mist flows) to be used to calculate the main stream flow rate. The homogenous mixing state is assumed to be maintained over some distance downstream of the main pipe flow meter 40, enabling the sampling probe to perform the desired isokinetic sampling.

Preferred embodiments of separate mixers or flow conditioners are described below.

Figure 5:
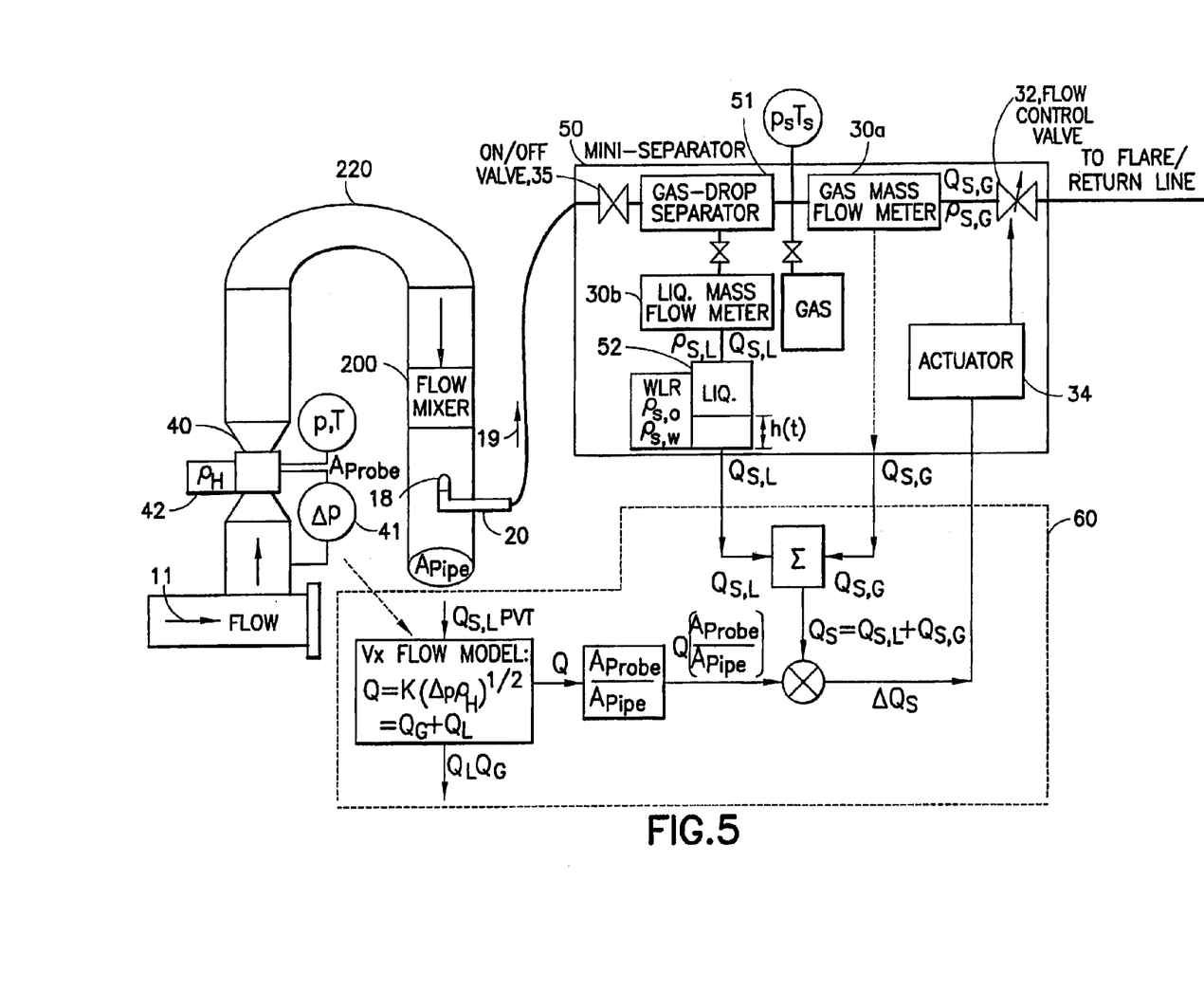
FIG. 5 is a schematic illustration of an isokinetic sampling system according to another embodiment of the present invention.

Another embodiment of the present invention is shown schematically in FIG. 5. An embodiment of the method of the present invention is also described in relation to this Figure. Again components which have already been discussed in relation to FIGS. 1 and 4 have the same reference numbers.

This embodiment has a flow meter 40 which combines a Venturi pressure drop measurement 41 with a gamma-ray densitometer 42. An example of such a meter is the PhaseTester/PhaseWatcher™ Vx Venturi meter described in SPE paper 77405 (by S. Jayawardane and B. C. Theuveny "PVT Sampling With Multiphase Flowmeters—Theoretical Justifications and Field Limitations", SPE Annual Technical Conference & Exhibition, San Antonio, Tex., 29 Sep. to 2 Oct. 2002). The pressure and temperature (p, T) of main flow stream 11 can also be measured at this point. The Vx flow meter has been shown (see SPE paper 76766) to give better multiphase flow rate measurement than a test separator, especially at high gas rate and/or unsteady flow conditions.

This embodiment uses a total mass flow rate measurement $Q = K\sqrt{\Delta p \cdot \rho_H}$, obtained from the combined measurements of high-energy mixture density ($\rho_H$, calculated to about 10 kg/m$^3$ accuracy by the Vx nuclear source) and $\Delta p$ from the Venturi measurement (calculated to within 1% accuracy) to set the extraction rate for isokinetic sampling, where K is a calibration factor depending on Venturi throat diameter, inlet diameter and the discharge coefficient; see, for example, eq.5 in SPE paper 77405. The mass flow rate error $$\frac{\Delta Q}{Q} = \frac{1}{2}\left[\frac{\Delta(\Delta p)}{\Delta p} + \frac{\Delta \rho_H}{\rho_H}\right]$$

is thus within 2.5% for a mixture density $\rho_H = 300$ kg/m$^3$.

The sampling probe 20 has an opening area (Aprobe), or ratio of its area to the pipe area ($A_{pipe}$), which is known accurately to within 2% and is maintained unchanged over a long period. To achieve this, the probe tip 18 is made from damage-resistant material such as tungsten carbide or cobalt alloy.

Consideration is also given to the size of the opening of the sampling probe tip 18. In order to keep the relative error in the area of the opening of the probe, or in the area ratio to within 2%, a 1% accuracy is required in the diameter of the opening of sampling probe 20. Therefore for a small opening diameter sampling probe 20 (e.g. 1.5 mm), the tolerance in diameter has to be very high (<15 µm). Increasing the opening diameter of the sampling probe 20, for example to 3 mm, reduces the demand on the machining tolerance for the probe (to <30 µm for the 3 mm example above). For high GLR flows, a larger probe size may also be beneficial as it will increase the amount of liquid sampled and therefore ease the sizing of the Coriolis mass flow meters 30a and 30b for use at higher ranges of gas and liquid flow rates in the mini-separator 50.

It is preferable to have a uniformly mixed wet-gas flow at the sampling cross section. This is achieved by placing a flow conditioner 200 upstream of sampling probe 20. Preferred embodiments of the flow conditioner 200 are described below.

It is also preferable that the stream at the Venturi portion of the Vx flow meter 40 is also homogenous wet-gas flow (i.e. with negligible gas-liquid slip), and so a further flow conditioner may be provided upstream of the Vx flow meter 40.

With the on/off valve 35 open and operating in conditions of well-mixed wet-gas flows in which there is low liquid mass (i.e. $Q_L/Q_G \ll 1$) the total mass flow rate measurement Q from the Vx flow meter 40 ($Q = K\sqrt{\Delta p \cdot \rho_H} = Q_G + Q_L = Q_G(1 + Q_L/Q_G)$) is first used to set an approximate 'dry' gas sample extraction mass flow rate $Q_{S,G_0} = (A_{probe}/A_{pipe}) \times Q$ by adjusting flow control valve 32 in the mini-separator 50 through use of the actuator 34.

The mass flow rate of the 'dry' gas sample flow $Q_{S,G}$, after gas-droplet separation in the gas-drop separator 51, can be directly measured using a Coriolis flow meter 30a.

The sampled liquid mass flow rate $Q_{S,L}$ is measured using an instrumented liquid collection system 52 in the mini-separator 50. Precise achievement of isokinetic sampling has less effect on the sample liquid mass flow rate $Q_{S,L}$ than on the sample gas flow rate because of the higher inertia of liquid droplets compared to the gas.

In the mini-separator 50 the sampled liquid mass flow rate $Q_{S,L}$ can be derived from the change in the liquid level over time h(t) in the liquid collection vessel 52 from a Dp level sensor (not shown) (p=$\rho_{S,L}$gh; $Q_{S,L}$=($A_L$/g)·(dp/dt)), where $A_L$ is the cross-sectional area of the liquid collection vessel 52).

However, in the embodiment illustrated in FIG. 5, $Q_{S,L}$ is also measured using a second Coriolis mass flow meter 30b, which also gives the liquid mixture density $\rho_{S,L}$. For example the second Coriolis mass flow meter 30b may be a Promass 80A™ Coriolis meter as made by Endress-Hauser. This meter can measure liquid mass flowrate to ±0.1%, gas mass flowrate to ±0.5% and density to ±1 kg/m³, and is reported to measure flow rates as small as 0.1 kg/h.

An extra linear array of MEMS (Micro Electro Mechanical Systems) densitometer can be installed along the height of the liquid collection vessel 52, allowing oil and water densities ($\rho_{S,O}$, $\rho_{S,W}$) to be determined from the separated oil-water interface profile at separator temperature and pressure ($T_S$, $p_S$).

It is preferable that the liquid is separated at line pressure not following a pressure reduction to minimize mass transfer between the phases. It is also preferable that the liquid sample mass flow rate measurement system, whether it is a Coriolis meter or a measurement bottle has an error of 2% or less to achieve good results in the closed-loop feedback system described below (a better than 2% accuracy is necessary to obtain an accurate measurement of the sampled liquid flow rate $Q_{S,L}$, and of the main-pipe liquid rate $Q_L$=($A_{pipe}$/$A_{probe}$)× $Q_{S,L}$).

The water cut ($\gamma_W$) can then be determined from the liquid mixture density relation $\rho_{S,L}$=$\gamma_W \rho_{S,W}$+(1-$\gamma_W$)$\rho_{S,O}$. Alternatively the water cut can be measured by other means, for example using microwave or optical sensors, such as the RedEye™ infrared water-cut meter from eProduction Solutions, Texas US, prior to complete separation of the liquids.

The first measure of the liquid sample mass flow rate $Q_{S,L}$ is then combined with the measured sample gas mass flow rate in the controller 60 to obtain the total sample mass flow rate $Q_S$. The controller 60 then compares this with the current main pipe total mass flow rate as measured by the main pipe flow meter 40. The sample extraction rate 19 is then varied as necessary by adjusting the flow control valve 32 in the mini-separator 50, through use of the actuator 34, so as to cause the sample mass flow rate to approach ($A_{probe}$/$A_{pipe}$)×Q, and thus isokinetic sampling conditions.

The above process can then be repeated for successive measurements of the total sample mass flow rate, thereby achieving convergence with the isokinetic sampling conditions. The process may be run effectively continuously throughout the sampling process, and thereby adjust the sampling flow rate as necessary when the flow of the main stream varies for any reason. In this respect, the term "continuous" includes repeated discrete applications of the measuring and correcting steps above at regular intervals, these intervals being shorter than the time scale over which significant changes in the total mass flow rate of the main stream occur. A typical interval is less than 30 sec, and preferably less than 10 or 5 sec.

For the maintenance of isokinetic sampling in this system, the existence of a pressure difference between the main pipe 220 and the mini-separator 50 does not affect the sampling. Mass transfer between the liquid and gas phases can occur without prejudicing the sampling control process since the process is based on total mass flows and not on the volume rate of a single phase.

However, it is preferable that the pressures in the mini-separator 50 and in the main pipe 220 are approximately equal, so that no mass transfers between the gas and liquid phases occur between the pipe and the separator. In this situation, the main pipe gas and liquid mass flow rates can be obtained as follows:

Total mass flow rate Q=K$\sqrt{\Delta p \cdot \rho_H}$, obtained from the Vx Venturi $\Delta p$ measurement and the high-energy mixture density $\rho_H$ measurement;

Liquid mass flow rate $Q_L$=($A_{pipe}$/$A_{probe}$)× $Q_{S,L}$, obtained from the isokinetic sampling;

Gas mass flow rate $Q_G$=Q-$Q_L$=Q-($A_{pipe}$/$A_{probe}$)× $Q_{S,L}$, preferably obtained from the Vx total flow measurement and isokinetic sampling, also obtainable purely from the isokinetic sampling as which can therefore be used as a quality control check.

As a result, the PVT relations are no longer required to convert the liquid mass flow rate measured at separator conditions ($p_S$, $T_S$) to that at main stream conditions (p, T) in order to obtain gas and liquid mass flow rates from the Vx measurements and interpretation models. However, PVT relations are required to convert the mass flow rates at line conditions (p, T) to volume flow rates at standard conditions.

The mini-separator 50 also provides the following measurements of the sampled flow:

Densities $\rho_{S,G}$, $\rho_{S,L}$, $\rho_{S,O}$, $\rho_{S,W}$ (of gas, liquid, oil and water samples respectively) obtained from the Coriolis gas and liquid flow meters 30a and 30b and the MEMS densitometer array reading from the liquid collection vessel 52;

Water cut $\gamma_W$=($\rho_{S,L}$-$\rho_{S,O}$)/($\rho_{S,W}$-$\rho_{S,O}$) calculated from the densities above;

GLR=($Q_{S,G}$/$\rho_{S,G}$)/($Q_{S,L}$/$\rho_{S,L}$) calculated from the separator gas and liquid volume flow rates;

Liquid mass loading m=$Q_{S,L}$/$Q_{S,G}$ calculated from the separator flow rates—ideally m<1 for a well mixed wet-gas regime which the system is being used to analyse; and PVT data from the samples obtained from the separated liquid flow and separated (i.e. 'dry') gas flow in the mini-separator 50.

Figure 6:
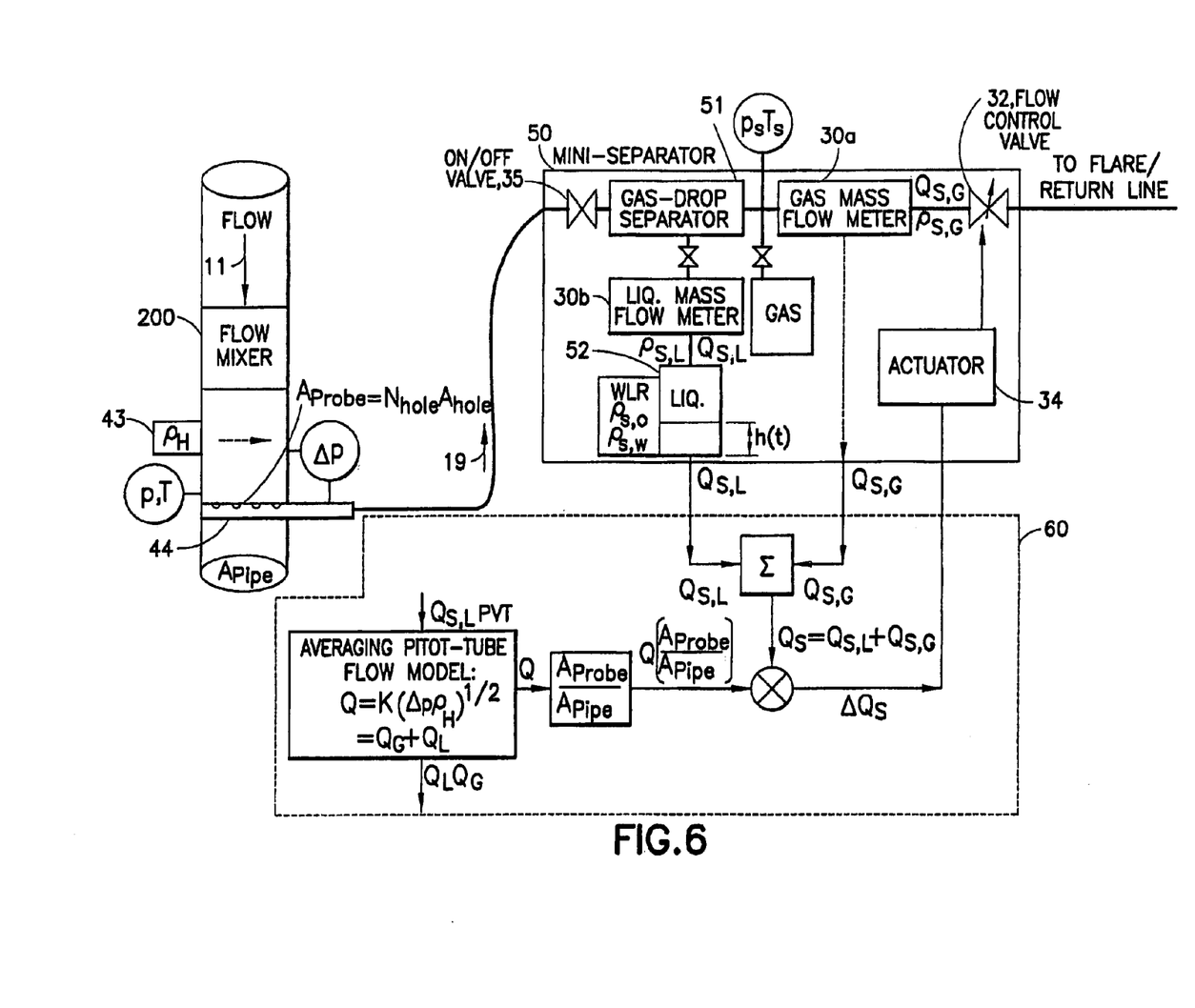
FIG. 6 is a schematic illustration of an isokinetic sampling system according to a further embodiment of the present invention.

Another embodiment of the apparatus and method of the present invention is illustrated schematically in and with reference to FIG. 6.

As with the embodiments described above, it is preferable that the wet-gas flow at the sampling cross-section is well-mixed, and this is achieved using mixer or flow conditioner 200 positioned upstream of the sampling cross-section. Again, preferred embodiments of the flow conditioner are described below.

An averaging Pitot-tube (APT) 44 is used to derive the main pipe total mass flow rate when operating at impact-pressure measuring (Pitot) mode, as well as a sampling probe. The APT 44 has multiple holes, for example four or six holes, specifically arranged along the diametrically aligned tubing. For example, for a six-hole probe the holes are preferably placed on the probe tubing at the following positions: -0.913R, -0.707R, -0.408R, +0.408R, +0.707R, +0.913R, where R is the radius of the pipe. The hole positions preferably correspond to the centres of the sampled equal area annuli of the pipe circular cross section. As with the previous embodiment, for sampling accuracy it is preferable that the area of the hole openings of the APT 44 ($A_{probe}$=$N_{hole}$× $A_{hole}$), relative to the pipe area $A_{pipe}$ at the sampling cross-section, is known to within 2% and does not change over the time of testing and sampling. This can be achieved by making the APT 44 from damage resistant material such as tungsten carbide or cobalt alloy.

One example of an APT is the Rosemount Probar™ insertion meter operating at impact-pressure measuring (Pitot) mode only, which claims a relative accuracy of ±1.1% in volumetric flow rate measurements for steam, liquid and gas. APTs can also be obtained from Thermocouple Instruments Ltd. Of Cardiff, UK.

An APT probe has very low pressure loss and generally costs less than a Venturi flow meter. The pipe averaging characteristics of the APT 44 reduce any variations in the cross-pipe flow at the sampling cross section.

A high energy gamma-ray densitometer 43 is installed upstream of the APT probe 44 and downstream of the flow conditioner 200 to obtain the density $\rho_H$. The densitometer 43 can have an accuracy within 10 kg/m$^3$ from a 30 mCi $^{137}$Cs source (with high energy gamma-ray at 661.66 KeV) and a NaI scintillation detector.

The APT 44 is first set to operate in normal impact pressure measurement mode, with on/off valve 35 set in the off position and with no sampling flow being taken. The APT measures the differential pressure $\Delta p$ across the main-pipe static pressure tap and the APT probe static pressure tap (typically to within 1% accuracy), and the main pipe total mass flow rate is calculated as $Q=K_1\sqrt{\Delta p \cdot \rho_H}$ (here $K_1$ is a calibration factor dependent on the probe geometry and flow Reynolds number).

The APT 44 is then switched to operate in sampling mode by opening the on/off valve 35 and by adjusting flow control valve 32 through actuator 34. The averaging nature of the APT 44 means that the main flow stream is sampled at multiple points across the diameter of the sampling cross section. Therefore variations in the cross-pipe GLR profile, which may be found downstream of an imperfect flow conditioner, can be largely overcome. Alternatively, when an APT is used, as in the current embodiment, the performance requirements of the flow conditioner can be made less stringent.

Operating in conditions of wet-gas flows in which there is low liquid mass (i.e. $Q_L/Q_G<1$) the total mass flow rate measurement Q from the gamma-ray densitometer 43 and the APT 44 operating in impact pressure measurement mode ($Q=K_1\sqrt{\Delta p \cdot \rho_H}=Q_G+Q_L=Q_G(1+Q_L/Q_G)$) is first used to set an approximate 'dry' gas sample extraction mass flow rate $Q_{S,G_0}=(A_{probe}/A_{pipe})\times Q$ by adjusting flow control valve 32 in the mini-separator 50.

The remainder of the sampling process is the same as that described in relation to FIG. 5 above. In particular the flow control valve 32 is adjusted via the actuator 34 so that the sampling flow 19 is substantially isokinetic with the main pipe flow stream 11.

In a further embodiment, a single-hole sampling probe 20, such as that used in the embodiment described in relation to FIG. 5 above, can also be set to operate in impact pressure mode by switching valve 35 off and measuring the differential pressure $\Delta p$ across a main pipe static pressure tap and a static pressure tap on the probe 20. This measurement of $\Delta p$ could then be used to derive an independent estimate of the main pipe total flow rate using the density $\rho_H$ measured by densitometer 42.

In a further embodiment, in applications where the probe pressure loss (i.e. from the probe opening to the probe pressure tap) is relatively small, the isokinetic sampling condition can be substantially achieved by nulling the $\Delta p$ described above by adjusting the sampled flow rate of the sampled portion through the use of flow control valve 32. In this embodiment, the $\Delta p$ signal can be used as a control signal to control actuator 34, thus avoiding the use of flow meters 40. Note that this embodiment can be adapted to either the single hole probe shown in FIG. 5 or the multiple hole pitot tube probe shown in FIG. 6.

Note that the multiple-hole pitot tube sampling embodiments described in connection with FIG. 6 can also be used in applications where the independent measurement is made using Vx type meters as described in connection with FIG. 5.

Figure 7:
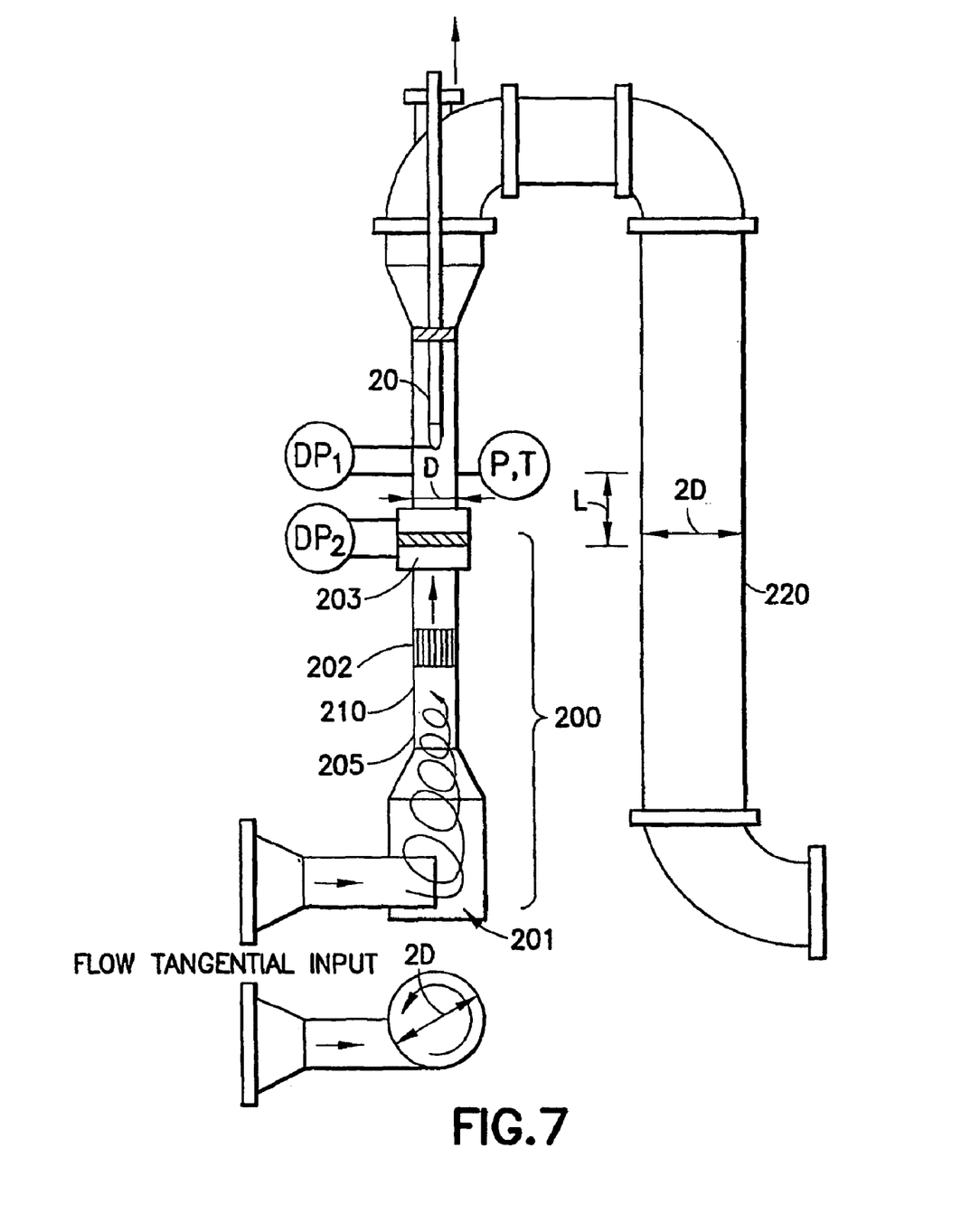
FIG. 7 is a schematic diagram of a flow conditioner according to an embodiment of the invention.

FIG. 7 is a diagram of a pipe section which is arranged to provide a relatively uniform cross-pipe profile at the sampling cross-section, particularly with regard to the GLR. The pipe section shown has a flow conditioner 200 for providing such a cross-section.

The flow conditioner 200 has three elements: a swirl inducing portion, which is provided in this embodiment by the tangential flow input 201; a gas flow core straightener 202; and an orifice plate 203.

The tangential flow input 201 causes the entire flow to swirl, thereby creating a substantially uniformly circumferentially distributed liquid film on the pipe wall 205. This removes variations due to the inflow conditions, such as non-axisymmetric gas and liquid flow distributions.

Figure 9:
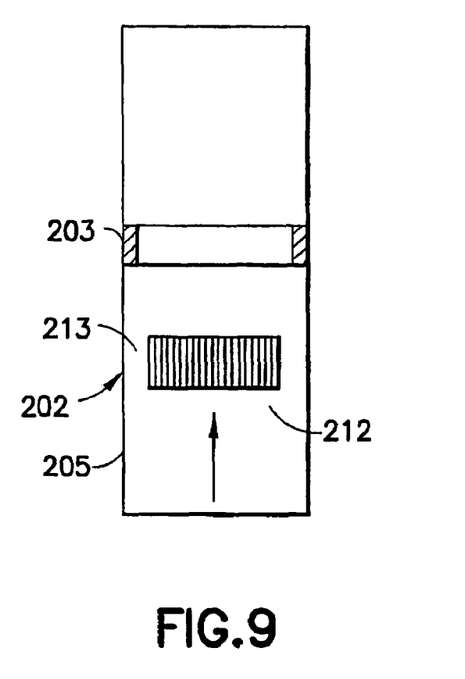
FIG. 9 is a schematic diagram of a flow straightener which may be used in the flow conditioners shown in FIGS. 7 and 8.

The core of the flow, which is mostly gas, is then straightened by the core straightener 202 positioned downstream of the tangential input 201. An example of such a core straightener 202 is illustrated in FIG. 9 and comprises a conventional straightener 212 (such as those described in U.S. Pat. No. 3,840,051, U.S. Pat. No. 5,309,946 and U.S. Pat. No. 5,762,107) positioned with an annular gap 213 between the straightener 212 and the pipe wall 205 so as not to interfere with the liquid flow along the pipe wall. The core straightener 202 removes the swirl in the central gas core of the flow, thereby reducing the amount of liquid re-deposited on the wall after the orifice plate mixing. This facilitates the obtaining of consistent gas-liquid flux profiles at the sampling cross-section.

Downstream of the core straightener 202, an orifice plate 203 is positioned, which causes the liquid film flowing on the pipe wall to be shed back into the now straightened gas core. The diameter β-ratio (the ratio of the open diameter of the orifice plate 203 to the diameter of the pipe) is preferably between 0.85 and 0.95. A further orifice plate (not shown) may be positioned downstream of orifice plate 203, and sheds any liquid film re-deposited on the wall after the orifice plate 203.

The liquid shed from the pipe wall by the orifice plate 203 is then subjected to an acceleration-induced catastrophic break-up by the gas flow which has a high axial velocity. In the region immediately downstream of the orifice plate 203, a liquid rich cone is formed at the centre of the flow. Downstream of this cone, the turbulent kinetic energy is high and hence the secondary turbulent break-up controls the droplet size distribution. Further downstream, as the turbulent kinetic energy decays quickly, turbulent break-up ends and coalescence effects determine the liquid droplet size. Thus the cross-pipe liquid flux distribution downstream of the orifice plate 203 is totally different from that upstream of the plate 203.

The sampling probe is preferably placed at an axial distance L downstream of the orifice plate 203, the distance L being chosen so as to avoid sampling at the liquid-rich core region caused by the shedding of the liquid film by the orifice plate 203, and to allow for some break-up due to turbulence and diffusion, leading to smaller drop sizes and more uniform cross-pipe GLR. The preferred values of L are 1D to 3D.

The use of an orifice-plate type mixer 203 is preferable to the flow-focusing type mixers, such as those disclosed in GB 2301297 and U.S. Pat. No. 5,894,080. An easy-to-machine orifice-plate mixer 203 serves to shed the liquid film from the pipe wall, which is then subjected to acceleration-induced catastrophic break-up by the incoming high axial-velocity gas flow. For a 4" pipe diameter (D=100 mm) down-flow example at low pressures, a much more uniform cross-pipe GLR has been experimentally measured 3D downstream of a single orifice-plate 203 with diameter ratio β=0.95 (see FIG. 2b) than that obtained with the flow-focusing mixer 15 shown in FIG. 2a (which is similar to that described in GB 2301297). As a result, the GLR error at the pipe centre is reduced by about five-fold over the flow-focusing type mixer shown in FIG. 2a. The orifice plate and the flow-focusing mixer were both tested at the same CGR of 60 bbl/MMscf, at a gas rate of 1.2 MMscf/day.

The embodiment of FIG. 7 shows the flow conditioner and sampling probe 20 implemented in a pipe section 210 of smaller diameter than the main pipe 220 (for example a section of 2 inch (D=50 mm) rather than 4 inch (100 mm) diameter). For a given mass flow rate of a well stream, deploying the sampling probe 20 at a small diameter pipe section 210 achieves the highest gas flow momentum ($\rho_G U_G^2$) and hence the highest gas Weber number $We_D = \rho_G U_G^2 D/\sigma$ (where σ is the surface tension). This may be beneficial as it: increases the shear for the liquid-film primary break-up from the wall, hence increasing drop formation; causes generation of small size droplets, thereby reducing the drop Stokes number and gas-drop velocity slip; increases the cross-pipe uniformity and the percentage of liquid entrainment.

Figure 8:
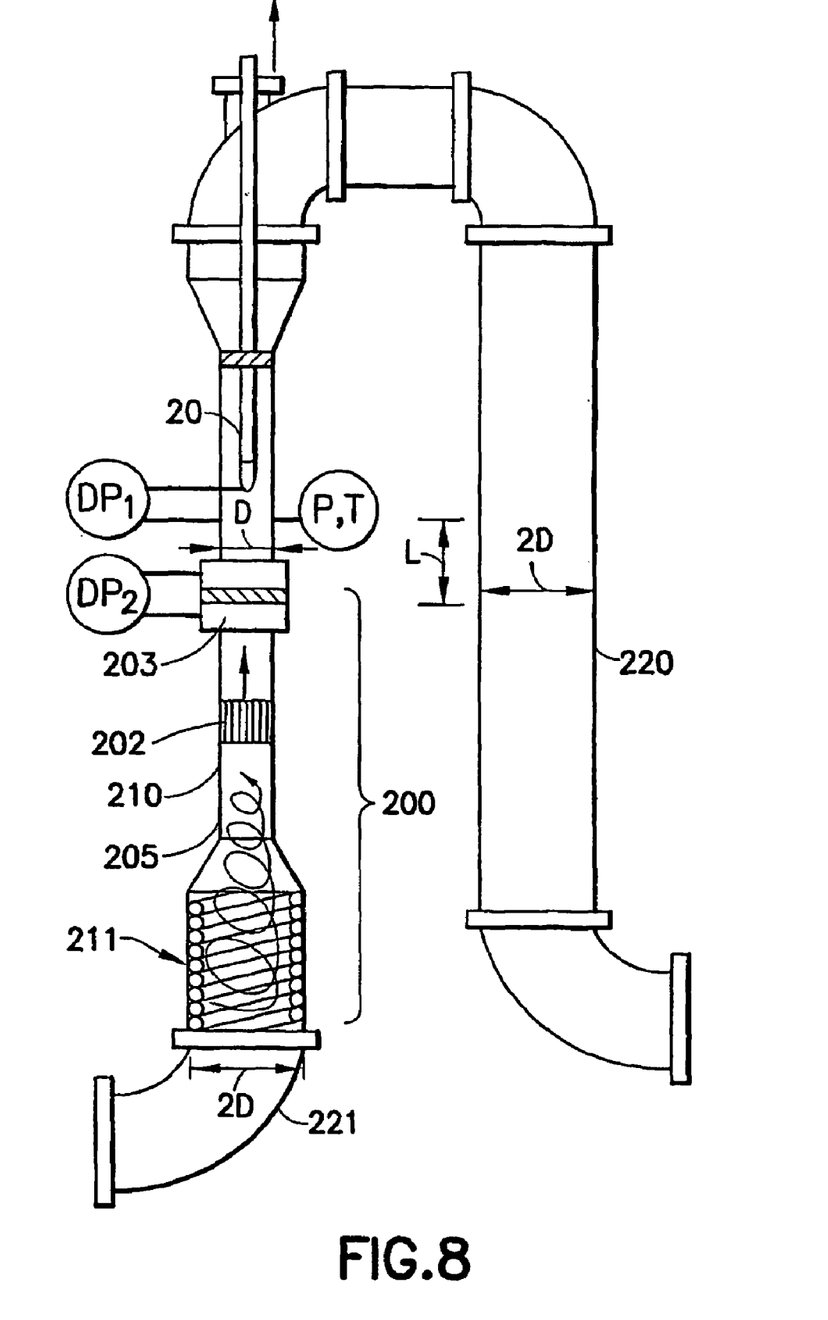
FIG. 8 is a schematic diagram of a flow conditioner according to an alternative embodiment of the invention.

An alternative embodiment of the flow conditioner 200 is shown in FIG. 8. This embodiment is the same as that in FIG. 6, except that the tangential input 201 has been replaced by a bend inlet 221 followed by a helical insert 211 to provide the initial swirl.

Alternative embodiments which cause axisymmetric distribution of the liquid film on the pipe wall, by causing swirl in other ways may also be used.

The above embodiments may form part of an overall sampling apparatus, being combined with the apparatuses and methods of earlier embodiments to provide a uniform cross-pipe GLR for sampling.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

The invention claimed is:

1. A method of sampling a multi-phase fluid stream comprising the steps of:
    sampling, with a sampling probe, a portion of the fluid stream;
    measuring the flow rate $Q_S$ of said sampled portion; and
    measuring, independently of the sampling step, the total flow rate Q of the fluid stream,
        wherein the flow rate of the sampled portion is controlled according to the ratio of the flow rate of the sampled portion to the flow rate of the fluid stream, in order to obtain substantially isokinetic sampling of the fluid stream, and
        wherein the step of controlling the flow rate of the sampled portion is carried out continuously during the sampling process.

2. A method according to claim 1 further including the step of separating said sampled portion into a sampled liquid flow and a sampled gas flow, and wherein said step of measuring the sampled flow rate includes measuring the flow rate of the sampled liquid flow and the flow rate of the sampled gas flow.

3. A method according to claim 1 wherein the step of measuring the total flow rate includes measuring the density of the fluid stream.

4. A method according to claim 1 wherein the step of measuring the total flow rate includes measuring a differential pressure.

5. A method according to claim 1 wherein the step of controlling the flow rate of the sampled portion is carried out continuously during the sampling process.

6. A method according to claim 1 wherein the fluid stream is a feed from a well-head.

7. A method according to claim 1 further including, prior to sampling the fluid stream, the step of conditioning the fluid stream.

8. A method according to claim 7, wherein said step of conditioning the fluid stream includes the sub-steps of successively:
    forming a liquid film at the wall of a pipe section which carries the fluid stream;
    straightening the flow of at least the core of the fluid stream; and
    shedding the liquid film into said core.

9. A method according to claim 8 wherein the sub-step of forming the liquid film includes causing the fluid stream to swirl about the axis of the pipe section.

10. Sampling apparatus for sampling a multi-phase fluid stream, comprising:
    means for measuring the total flow rate Q of the fluid stream;
    a sampling probe for sampling a portion of said fluid stream;
    a meter for measuring the flow rate $Q_S$ of said sampled portion, wherein the means for measuring the total flow rate is independent of the meter for measuring the flow rate $Q_S$ of said sampled portion; and
    a controller adapted to continuously control the flow rate of the sampled portion according to the ratio of the flow rate of the sampled portion to the total flow rate of the fluid stream, in order to obtain substantially isokinetic sampling of the fluid stream.

11. Apparatus according claim 10 further including a separator for separating said sampled portion into a sampled liquid flow and a sampled gas flow; a meter for measuring the flow rate of the sampled liquid flow; and a meter for measuring the flow rate of the sampled gas flow.

12. Apparatus according to claim 11 wherein either or both of said meters are Coriolis flow meters.

13. Apparatus according to any one of claim 11 wherein the means for measuring the total flow rate includes a densitometer for measuring the density of the fluid stream.

14. Apparatus according to any one of claim 11 wherein the means for measuring the total flow rate includes a differential pressure sensor.

15. Apparatus according to claim 14 wherein said differential pressure sensor is for use with a Venturi meter.

16. Apparatus according to claim 14 wherein said differential pressure sensor is for use with a Pitot tube.

17. Apparatus according to claim 10 further including, upstream of said sampling probe, a flow conditioner.

18. Apparatus according to claim 17 wherein said flow conditioner is a pipe section including:
   a swirl inducing section;
   a flow straightener; and
   an orifice plate.

19. Apparatus according to claim 18 wherein said swirl inducing section includes a tangential input to the pipe section.

* * * * *